(12) United States Patent
Park et al.

(10) Patent No.: US 9,017,719 B2
(45) Date of Patent: Apr. 28, 2015

(54) INJECTABLE DRUG CARRIER COMPRISING LAYERED DOUBLE HYDROXIDE

(75) Inventors: Taeun Park, Seoul (KR); Jin-Ho Choy, Seoul (KR); Jae-Min Oh, Seoul (KR); Ji-Sun Jung, Seoul (KR)

(73) Assignee: Nanohybrid Co., Ltd., Seoul (KR)

( * ) Notice: Subject to any disclaimer, the term of this patent is extended or adjusted under 35 U.S.C. 154(b) by 0 days.

(21) Appl. No.: 13/541,413

(22) Filed: Jul. 3, 2012

(65) Prior Publication Data

US 2012/0276170 A1 Nov. 1, 2012

Related U.S. Application Data

(63) Continuation of application No. 11/915,922, filed as application No. PCT/KR2005/001667 on Jun. 3, 2005, now abandoned.

(30) Foreign Application Priority Data

Jun. 2, 2005 (KR) .................. 10-2005-0047235

(51) Int. Cl.
 *A61K 9/127* (2006.01)
 *A61K 9/00* (2006.01)
 *A61K 9/14* (2006.01)
 *A61K 47/02* (2006.01)

(52) U.S. Cl.
 CPC .............. *A61K 9/0019* (2013.01); *A61K 9/143* (2013.01); *A61K 47/02* (2013.01)

(58) Field of Classification Search
 USPC ....................................................... 424/450
 See application file for complete search history.

(56) References Cited

U.S. PATENT DOCUMENTS

| 5,242,921 A | * | 9/1993 | Milstone et al. ............... 514/249 |
| 5,648,097 A | | 7/1997 | Nuwayser |
| 5,846,952 A | | 12/1998 | Vournakis et al. |
| 5,904,718 A | | 5/1999 | Jefferies |

(Continued)

FOREIGN PATENT DOCUMENTS

| KR | 1020000019408 A | 4/2000 |
| KR | 1020030014182 A | 2/2003 |

(Continued)

OTHER PUBLICATIONS

Choy et al (Biomaterials 25 (2004) 3059-3064).*

(Continued)

*Primary Examiner* — Benjamin Packard
(74) *Attorney, Agent, or Firm* — Rothwell, Figg, Ernst & Manbeck, P.C.

(57) ABSTRACT

Provided is an injectable drug carrier including a non-toxic Layered Double Hydroxide (LDH) and pharmaceutically acceptable excipients. Provided is also a method of preparing the injectable drug carrier, the method including: synthesizing LDH with various compositions and controlling the size and shape of the LDH at a level that the LDH has no adverse effect in vivo. A solution obtained by dispersing the LDH in a solvent is injected in vivo. According to the method, nano-size LDH that does not affect a blood vessel in vivo can be synthesized. The LDH thus synthesized has no adverse effect in vivo even at a concentration of 400 mg/kg, and thus can contribute to establishment of a drug delivery system capable of improving the delivery efficiency of a specific drug.

7 Claims, 6 Drawing Sheets

(56) References Cited

U.S. PATENT DOCUMENTS

| | | |
|---|---|---|
| 6,329,515 B1 | 12/2001 | Choy et al. |
| 6,361,780 B1 | 3/2002 | Ley et al. |
| 6,558,703 B1 | 5/2003 | Karlsson et al. |
| 6,852,670 B1 | 2/2005 | Ogawa et al. |

FOREIGN PATENT DOCUMENTS

| | | |
|---|---|---|
| KR | 1020050010610 A | 1/2005 |
| KR | 1020050031501 A | 4/2005 |
| WO | WO9407468 A1 | 4/1994 |
| WO | WO9951278 A1 | 10/1999 |
| WO | WO0059629 A1 | 10/2000 |

OTHER PUBLICATIONS

ScienceDirect.com (http://www.sciencedirect.com/science/article/pii/S0142961203008500#, accessed Dec. 15, 2012).*

Kralj et al (Medicine on a small scale, EMBO reports vol. 4, No. 11, 2003, 1008-1012).*

"Controlled Tailoring of DNA chain length through DNA/LDH Nanohybrid System" (Symposium C: Bio-Inspired Nanoscale Hybrid Systems, Nateruaks Research Society, 2003).*

Y. Zhao et al.: "Preparation of Layered Double-Hydroxide Nanomaterials with a Uniform Crystallite Size Using a New Method Involving Separate Nucleation and Aging Steps," Chem. Mater., vol. 14, 2002, pp. 4286-4291.

* cited by examiner

INJECTABLE DRUG CARRIER COMPRISING LAYERED DOUBLE HYDROXIDE

CROSS-REFERENCE TO RELATED PATENT APPLICATION(S)

The present application is a continuation of U.S. patent application Ser. No. 11/915,922, filed on Nov. 29, 2007, which is a 35 U.S.C. §371 National Phase Entry Application from PCT/KR2005/001667, filed Jun. 3, 2005, and designating the United States and claims the benefit of Korean Patent Application No. 10-2005-0047235, filed on Jun. 2, 2005, in the Korean Intellectual Property Office, the disclosure of which are incorporated herein in their entireties by reference.

BACKGROUND OF THE INVENTION

1. Field of the Invention

The present invention relates to a use of Layered Double Hydroxide (LDH) as a drug carrier, and more particularly, to a method of loading a drug onto the LDH drug carrier, a method of improving drug delivery efficiency using the LDH drug carrier, and establishment of a safe dose range of LDH that has no adverse effect in vivo when LDH is administered through injection.

2. Description of the Related Art

Generally, currently available medications have possibility of destroying normal cells as well as diseased cells. Thus, many drugs are limitedly used. There also exist drugs that cannot be used in actual medication due to poor stability in spite of good medicinal activity. In addition, since a single dose is consumed rapidly in the human body during medication, some drugs have inconvenience to be administered several times. In view of these problems of existing drugs, various drug delivery systems capable of assuring good drug delivery efficiency, stability and controlled release rate have been developed.

Basic requirements of drug delivery systems variously depend on desired objectives. Preferentially, drug delivery systems must satisfy the following requirements: 1) drug stability, 2) drug targeting to a specific tissue, 3) regulation of drug release rate and 4) in vivo safety of delivery carriers. Development of organic, inorganic, or polymer drug delivery systems, etc. satisfying these various requirements has been carried out. Internationally developed drug delivery systems are as follows. U.S. Pat. No. 6,361,780, entitled "Microporous Drug Delivery System", discloses a drug delivery device using porous inorganic oxides, metals, etc. International Patent WO9407468, entitled "Two Phase Matrix for Sustained Release Drug Delivery", discloses a polymer-silicate phase-based drug delivery system for use as a transdermal patch. U.S. Pat. No. 6,558,703, entitled "Porous Hydroxyapatite Particles as a Carrier for Drug Substances", discloses a drug delivery system for oral administration which utilizes porous inorganic particles loaded with a sticky/greasy/oily drug substance. U.S. Pat. No. 5,846,952, entitled "Methods and Compositions for Poly-, Beta-, -1-4-N-Acetyl Glucosamine Drug Delivery", discloses poly-β-1→4-N-acetylglucosamine (p-GlcNAc) polysaccharide as a drug delivery system. In addition, U.S. Pat. No. 5,904,718, entitled "Delayed Drug Delivery System", discloses a sustained release drug delivery system using inorganic materials. U.S. Pat. No. 5,648,097, entitled "Calcium Mineral-Based Microparticles and Method for the Production thereof", discloses biodegradable inorganic calcium salt particles used as a drug carrier capable of controlling a drug release rate in the human body. European Patent No. EP1,067,971, entitled "Inorganic Materials for Radioactive Drug Delivery", discloses an inorganic drug delivery system. Recently, Korean Patent No. 10-0359715, entitled "Bio-inorganic Hybrid Complexes as Gene Reservoir and Potential Delivery Carrier and their Preparation", and U.S. Pat. No. 6,329,515, entitled "Bio-inorganic Compound Capable of Stable, Solid-State Storage of Genes and Preparation thereof", disclose that Layered Double Hydroxide (LDH) has the possibility of serving as a reservoir which safely stores DNAs and serving as a gene or drug delivery carrier. In addition, Korean Patent Application No. 2003-00676, entitled "Method of Preventing the Proliferation of Tumor Cells Using MTX-LDH Hybrid", discloses the prevention of proliferation of osteosarcoma cells using LDH incorporated with MTX which is an anticancer agent.

As described above, research and study on drug delivery systems have been currently actively carried out. In particular, research on drug delivery systems capable of controlling drug stability and release characteristics using polymers or inorganic materials has been most actively carried out. Research on drug delivery systems which increase drug efficacy at a cellular level is also carried out. However, drug delivery systems which is able to be directly used in vivo have not been sufficiently studied. In particular, injectable inorganic drug delivery carriers have been hardly studied.

The present invention is directed to a preparation of a LDH as a drug carrier capable of maximizing in vivo drug delivery efficiency and a use of it in an injectable formulation.

LDH, which is also called "hydrotalcite-like compound", is a compound having a similar structure to magnesium (Mg)-aluminum (Al) layered double hydroxide known as hydrotalcite, wherein magnesium or aluminum can be substituted by other divalent or trivalent metal. The LDH structure consists of positively charged hydroxide layers due to the presence of trivalent metal ions in substitution of divalent metal ions, and thus various anions can be intercalated between the positively charged hydroxide layers. Thus, a complex obtained by the intercalation of a negatively charged drug between the hydroxide layers of LDH can be used as a drug delivery system. Most of negatively charged drugs can be used herein, which includes various drugs such as methotrexate, vitamins (e.g., vitamin C or retinoic acid), genes with a negatively charged phosphate group, and antisense for gene therapy. It is anticipated that when administered in vivo through injection, LDH containing a negatively charged drug will provide advantages such as drug stability, sustained drug release, and improved drug delivery efficiency, with no harmful side effects along with pharmacological activity.

The present invention relates to the hybridization of nanotechnology and biotechnology. LDH used herein as an injectable drug carrier is an inorganic solid compound and is applied in various fields, including catalysts, supports, thermal stabilizers, antacids, etc. Depending on the purpose of LDH in these applications, metal composition, particle shape, particle size, etc. must be diversely controlled. Such a control belongs to the category of nanotechnology since it requires microscale or nanoscale particle control and molecular or atomic level modification in composition or physical property. Also for the intercalation of a physiologically active drug molecule into LDH, the interaction between the drug molecule and the LDH is to be controlled. Thus, the present invention also relates to a novel technology which converges medical technology, biotechnology, and nanotechnology. The present invention also relates to biotechnology in the respect that drug efficacy is evaluated after a drug delivery carrier is injected in vivo. Therefore, the present invention is a novel technology that can be accomplished by fusioning nanotechnology and biotechnology.

SUMMARY OF THE INVENTION

The present invention provides a non-toxic, injectable inorganic drug delivery system using Layered Double Hydroxide (LDH) with an appropriate physicochemical property as a drug carrier.

In view of the above objectives of the present invention, there is provided an injectable drug carrier including a non-toxic Layered Double Hydroxide (LDH) and a pharmaceutically acceptable excipients. LDH has possibility of having an adverse effect in vivo since the control of its size and shape is difficult. Furthermore, it has not been determined whether LDH is toxic or non-toxic in vivo because the LDH has not been administered through injection. However, the present inventors found that LDH was non-toxic and had no harmful side effects in vivo when administered through injection and thus first demonstrated that LDH could be used as an injectable drug carrier.

The present invention is characterized in that the LDH of particle size of 100 to 300 nm is preferred.

The present invention also provides a method of preparing an injectable drug carrier, the method which includes titrating a divalent and trivalent metal salts-containing aqueous solution with a base solution, incubating the resultant solution at room temperature or under hydrothermal synthesis condition to obtain LDH; and controlling a particle size of the LDH. Here, the "hydrothermal synthesis" refers to a synthesis method performed at a temperature higher than the boiling point of water (100° C.) in a hermetically sealed reactor under a vapor-phase pressure greater than atmospheric pressure.

In the present invention, the divalent metal may be selected from the group consisting of magnesium ($Mg^{2+}$), calcium ($Ca^{2+}$), and zinc ($Zn^{2+}$), the trivalent metal may be selected from the group consisting of aluminum ($Al^{3+}$) and iron ($Fe^{3+}$), and the base solution may be selected from the group consisting of sodium hydroxide (NaOH) and ammonia ($NH_3$).

The present invention also provides an injectable drug delivery system including the injectable drug carrier and a drug. Here, the drug may be any negatively charged drug that can be intercalated between hydroxide layers of LDH. Examples of the drug include various drugs such as methotrexate, vitamins (e.g., vitamin C or retinol acid), genes with a negatively charged phosphate group, and antisense for gene therapy. The drug can be loaded in the LDH by a method previously well known in the art, e.g., ion exchange or coprecipitation.

An injectable drug delivery system according to an embodiment of the present invention can be prepared by 1) synthesizing LDH with various compositions and controlling the size and shape of the LDH at a level suitable for use in a drug delivery system, and 2) processing the LDH into an injectable formulation.

Generally, LDH is synthesized by titrating a divalent and trivalent metal salts-containing solution with a base solution. The divalent metal may be magnesium ($Mg^{2+}$), calcium ($Ca^{2+}$), or zinc ($Zn^{2+}$), the trivalent metal may be aluminum ($Al^{3+}$) or iron ($Fe^{3+}$), and the base solution may be sodium hydroxide (NaOH) or ammonia ($NH_3$). LDH synthesized by precipitation can be obtained in the form of particles with desired composition, shape, and size by adjusting the concentration and ratio of metal ions, the titration rate, the total reaction time, etc. Preferably, LDH may be processed into fine particles with a particle size of 300 nm or less to prevent clogging of capillary blood vessels and to eliminate a physical impact when administered in vivo through injection. In the present invention, incubation for 24 hours after titration of NaOH solution into the solution containing magnesium and aluminum ions can produce uniform LDH particles.

The loading of a drug into LDH can be performed by ion exchange or coprecipitation. According to the ion exchange method, ions such as nitrate ($NO_3^-$), chloride ($Cl^-$), or carbonate ($CO_3^{2-}$) in the interlayers of LDH are substituted by ionized drug molecules. According to the coprecipitation method, ionized drug molecules are added to a mixed metal solution during titration, and encapsulation of the drug molecules occurs simultaneously with formation of LDH. Most of negatively charged drugs can be intercalated into LDH. Examples of the drug include various drugs such as methotrexate, vitamins (e.g., vitamin C or retinoic acid), genes with a negatively charged phosphate group, and antisense for gene therapy.

A drug-loaded LDH, i.e., a drug-LDH hybrid complex is represented by formula 1 below:

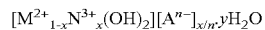

$$[M^{2+}_{1-x}N^{3+}_x(OH)_2][A^{n-}]_{x/n} \cdot yH_2O$$

wherein $M^{2+}$ is a divalent metal cation selected from the group consisting of $Mg^{2+}$, $Ni^{2+}$, $Cu^{2+}$, and $Zn^{2+}$, $N^{3+}$ is a trivalent metal cation selected from the group consisting of $Al^{3+}$, $Fe^{3+}$, $V^{3+}$, $Ti^{3+}$ and $Ga^{3+}$, x is 0.1 to 0.4, A is an anionic drug, n is a charge number of the drug, and y is a positive number.

In formula 1, the x related to a metal composition ratio may range from 0.1 to 0.4, and more preferably from 0.25 to 0.33. If the x value is outside of this range, encapsulation of a drug in LDH carrier, i.e., the intercalation of a drug between the hydroxide layers of the LDH carrier may not occur, which renders the production of a desired drug-LDH hybrid difficult.

The drug-LDH hybrid of the present invention may be used in a hydrate form. The degree of hydration can be expressed as the y value. The y value can be changed according to various factors such as moisture content in air, and can be represented by a positive number since it can be generally selected within a broad range.

LDH thus synthesized is dispersed in distilled water and further diluted with injectable distilled water. A finally obtained LDH-containing solution is injected intraperitoneally to Balb/c mice, and a change in body weight of mice and a death rate are measured for a month to evaluate an effect (e.g., toxicity) of LDH in vivo.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

According to the present invention, Layered Double Hydroxide (LDH) can be used as a biocompatible injectable drug carrier that has little toxicity and adverse effect in vivo. Furthermore, LDH can also be used as a non-toxic injectable drug carrier maximizing drug efficacy and drug delivery efficiency when it is injected in vivo in the form of a hybrid with various drugs. In addition, LDH is suitable for use as an injectable drug carrier with regard to a particle size and shape. An actual animal test shows that LDH has no adverse effect in vivo on intraperitoneal application.

Hereinafter, the present invention will be described more specifically with reference to the following examples. The following examples are for illustrative purposes and are not intended to limit the scope of the invention.

EXAMPLE 1

Synthesis of Layered Double Hydroxide (LDH)

Figure 1:
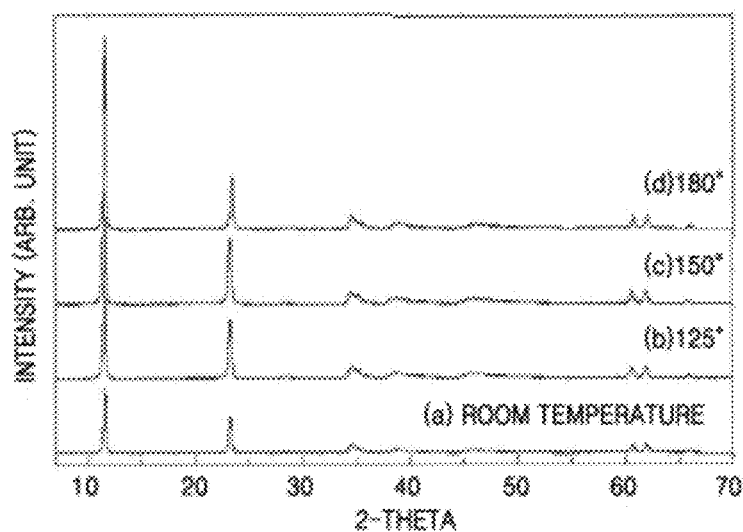
FIG. 1 is X-ray diffraction patterns of Layered Double Hydroxides (LDHs) synthesized at room temperature (a), and hydrothermally synthesized at 125, 150, and 180° C. (b, c, and d)
Figure 2A:
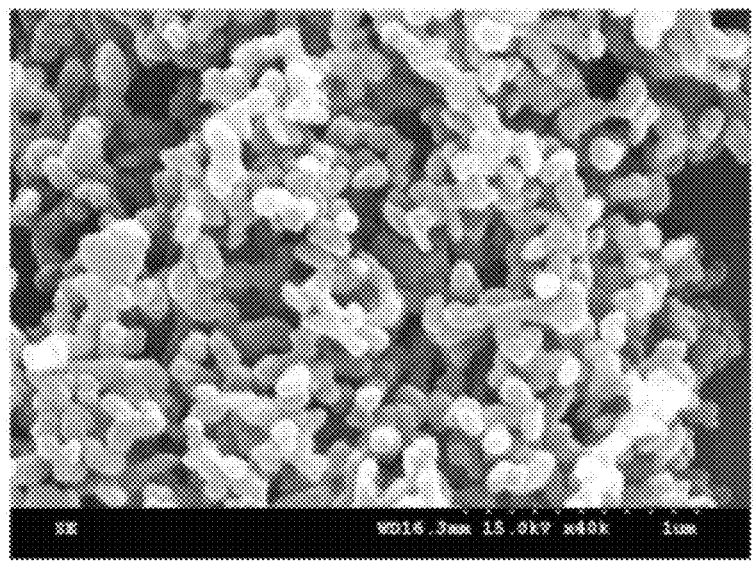
FIG. 2A is a Scanning Electron Microscope (SEM) image of LDH synthesized at room temperature.
Figure 2B:
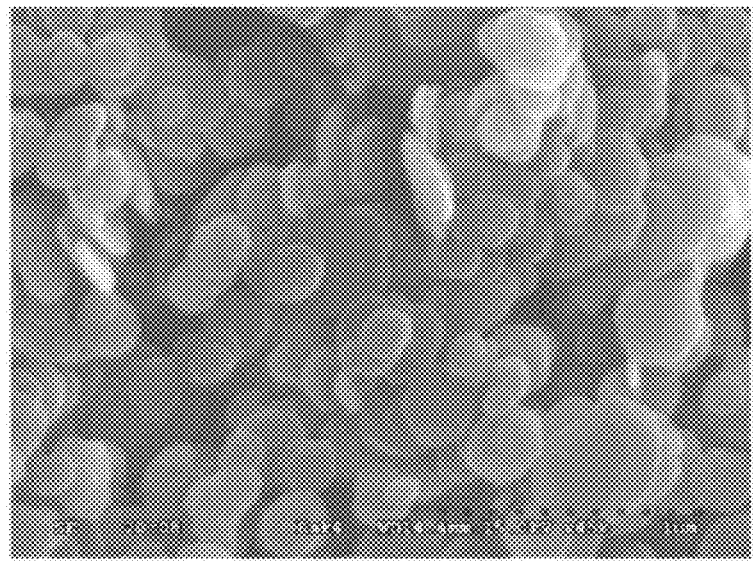
FIGS. 2B, 2C, and 2D are SEM images of LDHs hydrothermally synthesized at 125° C., 150° C., and 180° C., respectively.
Figure 2C:
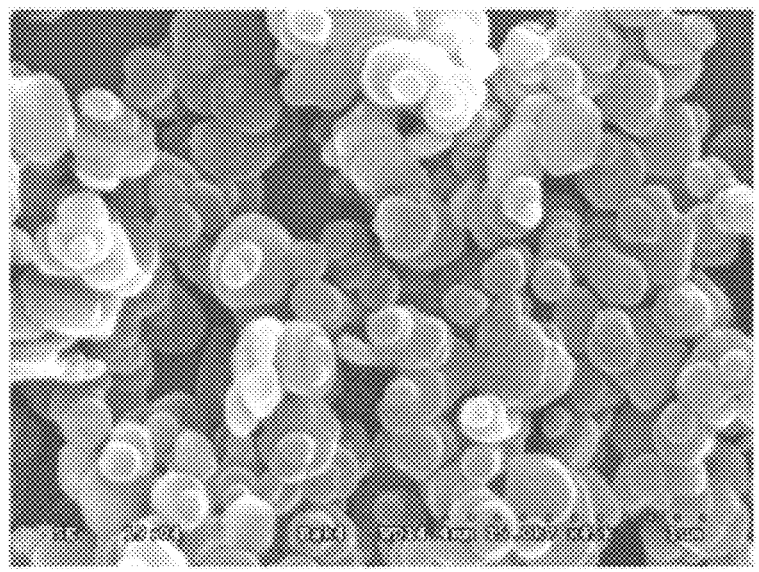
Figure 2D:
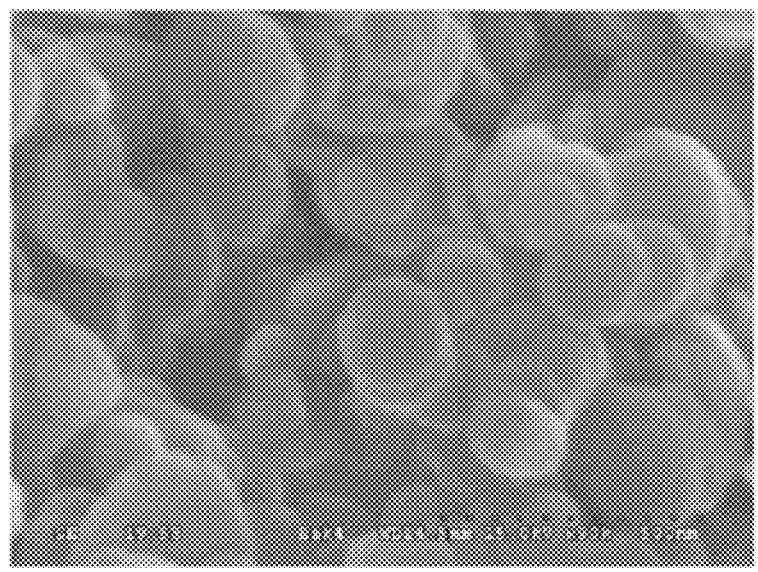

LDH's were synthesized as follows. A mixture of magnesium nitrate and aluminum nitrate (2:1) was dissolved in distilled water and sodium carbonate was then added in an amount of 1.5 times of the molar ratio of aluminum. The reaction solution was titrated with a 0.5 M sodium hydroxide solution until pH was 9.5. Then, some samples of the resultant solution were incubated at room temperature for 24 hours and some samples were incubated at 125, 150, and 180° C. under hydrothermal synthesis condition for 24 hours. X-ray diffraction patterns of LDH's thus obtained are shown in FIG. 1 and Scanning Electron Microscope(SEM) images showing particle shape and size are shown in FIG. 2. In FIG. 1, (a) is an X-ray diffraction pattern of the LDH synthesized at room temperature, (b), (c), and (d) are X-ray diffraction patterns of the LDHs hydrothermally synthesized at 125, 150, and 180° C., respectively. FIG. 2a is a SEM image of the LDH synthesized at room temperature, and FIGS. 2b, 2c, and 2d are SEM images of the LDHs hydrothermally synthesized at 125° C., 150° C., and 180° C., respectively. Referring to FIGS. 1, 2a, 2b, 2c, and 2d, the hydrothermally synthesized LDHs had a particle size ranging from 100 to 300 nm, which did not greatly depend on temperature. Thus, it can be seen that it is efficient to synthesize LDH at a low temperature (100-125° C.) if possible.

EXAMPLE 2

In Vivo Toxicity Test of LDH

Small animal models, Balb/c mice (6-7 weeks old) were purchased and managed in cages (5 mice/cage). The LDH synthesized by hydrothermal process at 125° C. as described in Example 1 was administered intraperitoneally to 10 mice at each concentration of 100, 200, 300, and 400 mg per 1 kg of body weight. The body weight of each mouse was measured prior to administration, and every week for three weeks, and a dose of the drug adjusted according to newly measured weight was administered.

Figure 3:
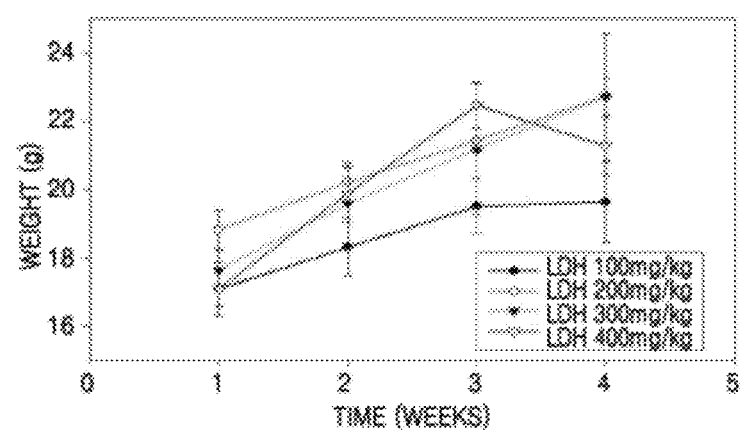
FIG. 3 is a graph illustrating a change in body weight of mice with respect to the concentration of LDH administered to mice intraperitoneally.

A change in the average of body weight of the 10 mice is shown in FIG. 3, and the body weights of the mice died during the test were excluded from statistical analysis. As shown in FIG. 3, weight loss was not observed even when a LDH level was 0.4% of the body weight (400 mg/kg). Rather, a gradual increase in body weight was observed. This shows that the mice grew normally.

Figure 4:
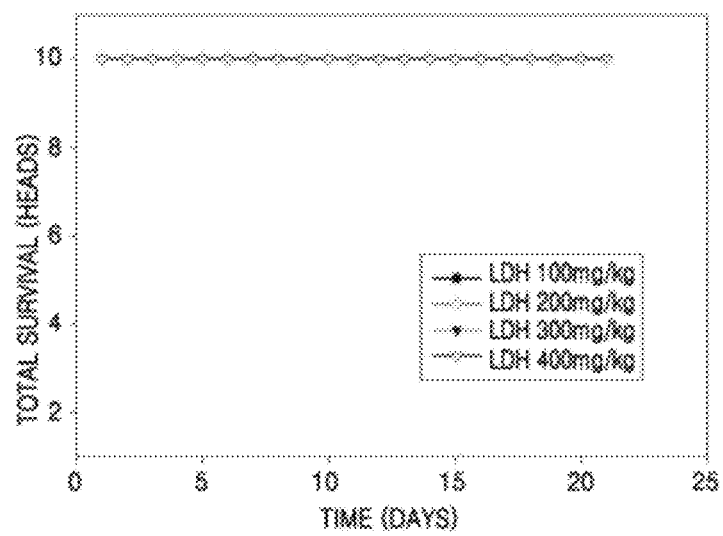
FIG. 4 is a graph illustrating the total survival of mice with respect to the concentration of LDH administered to the mice intraperitoneally.

In FIG. 4, the death rate of the mice with respect to the concentration of administered LDH is represented by total number of mice survived. As shown in FIG. 4, only one mouse died upon administration of 200 mg/kg of LDH for three weeks, and all mice were alive upon administration of 300 and 400 mg/kg of LDH for three weeks. This shows that LDH has no adverse effect in vivo even at a concentration of 400 mg/kg and thus can be used as an injectable drug carrier up to this dosage level.

EXAMPLE 3

Synthesis of LDH-MTX (Methotrexate) Hybrid

Figure 5:
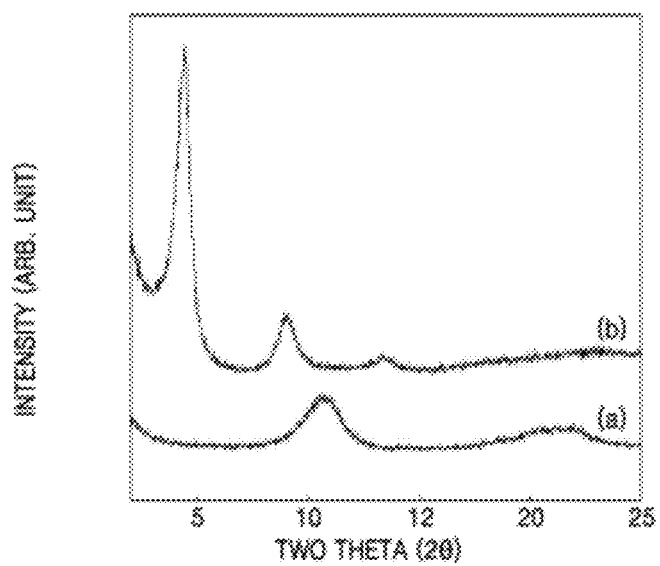
FIG. 5 is X-ray diffraction patterns of (a) LDH and (b) a LDH-methotrexate (MTX) hybrid synthesized by ion exchange.

To synthesize a hybrid of LDH and MTX, the LDH synthesized at room temperature in Example 1 was filtered with a filter of pore size of 450 nm and then dispersed in an excess MTX-containing solution at 60° C. under a nitrogen atmosphere for four days (ion exchange method). The LDH-MTX hybrid thus synthesized was washed with distilled water and dried in vacuum. The termination of the synthesis was confirmed by X-ray diffraction analysis. In FIG. 5, (a) is an X-ray diffraction pattern of LDH and (b) is an X-ray diffraction pattern of the LDH-MTX hybrid.

EXAMPLE 4

Anticancer Effect and in Vivo Toxicity Test of LDH-MTX Hybrid

Figure 6A:
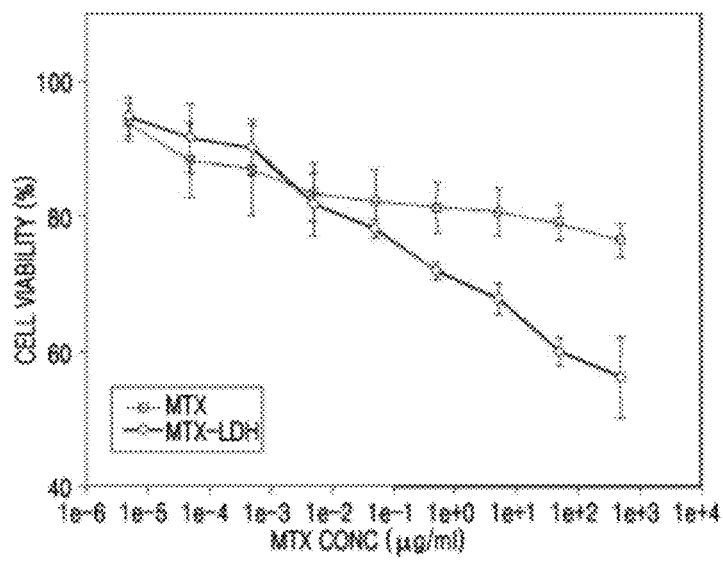
FIG. 6a is a graph illustrating cell viability with respect to the concentration of MTX and a LDH-MTX hybrid 24 hours after osteosarcoma cell line, SAOS-2, was treated with the MTX and the LDH-MTX hybrid
Figure 6B:
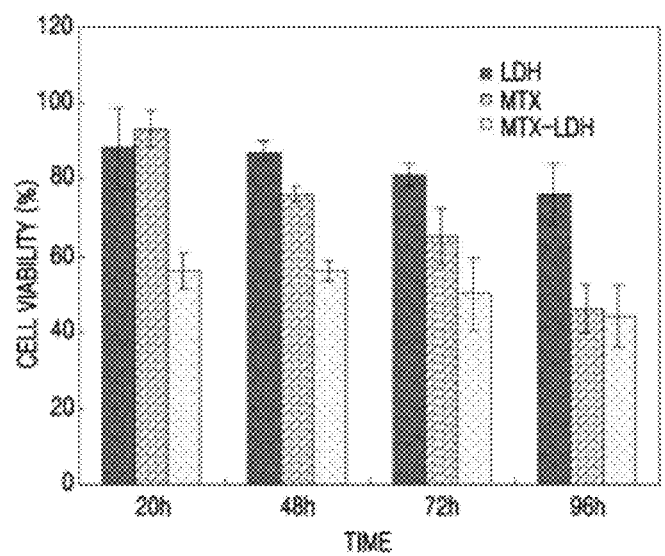
FIG. 6b is a graph illustrating cell viability with respect to the time after osteosarcoma cell line, SAOS-2, was treated with LDH, MTX, and a LDH-MTX hybrid (each at a concentration of 500 μg/ml)

An anticancer effect of the LDH-MTX hybrid relative to MTX was evaluated on human osteosarcoma cell lines, SAOS-2. An anticancer effect was evaluated using MTT [MTT: 3-(4,5-dimethylthiazol-2-yl)-2,5-diphenyl tetrazolium bromide] assay. The concentration of each MTX and LDH-MTX hybrid used was as follows: $5\times10^{-6}$, $5\times10^{-5}$, $5\times10^{-4}$, $5\times10^{-3}$, $5\times10^{-2}$, $5\times10^{-1}$, 5, 50, and 500 μg/ml. Cell viability with respect to each concentration at 24 hours after administration is illustrated in FIG. 6a, and cell viability with respect to the time after administration with LDH, MTX, and the LDH-MTX hybrid (each at a concentration of 500 μg/ml) is illustrated in FIG. 6b. Referring to FIG. 6a, the LDH-MTX hybrid exhibited the same anticancer effect as pure MTX even when administered at a lower concentration than that of MTX, and in particular, reached a maximal anticancer effect in a short time. This shows that LDH can be used as a carrier for an anticancer agent unless toxicity of LDH is a problem in vivo.

EXAMPLE 5

In Vivo Toxicity Test of LDH-MTX Hybrid

Figure 7A:
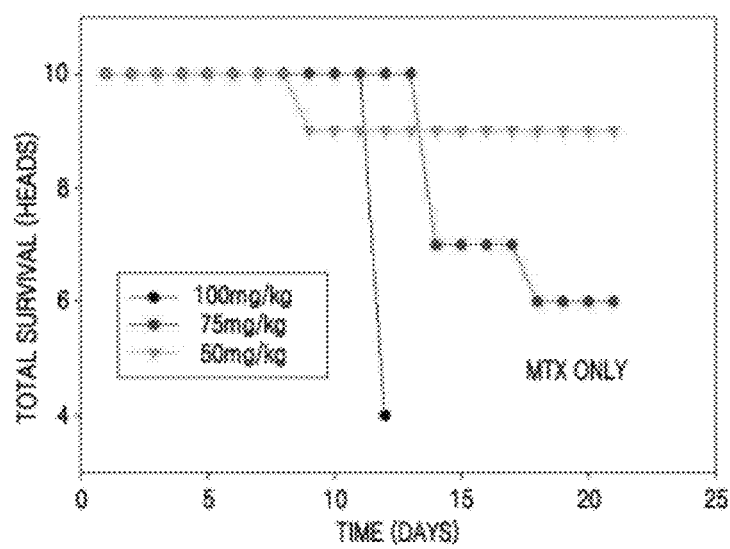
FIG. 7 is a graph illustrating the total survival of mice with respect to the concentration of MTX (7a) and a LDH-MTX hybrid (7b) administered to the mice intraperitoneally.
Figure 7B:
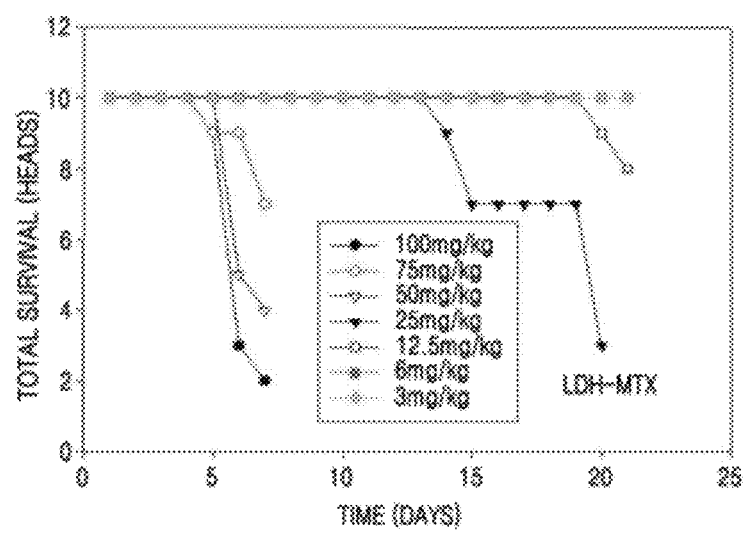

Like in the in vivo toxicity test of LDH of Example 2, small animal models, Balb/c mice (6-7 weeks old) were purchased and managed in cages (5 mice/cage). MTX was administered intraperitoneally to 10 mice at each concentration of 50, 75, and 100 mg/kg and the LDH-MTX hybrid synthesized in Example 3 was administered intraperitoneally to 10 mice at each concentration of 3, 6, 12.5, 25, 50, 75, and 100 mg/kg. The body weight of each mouse was measured every week for three weeks and a dosage of drug adjusted to the newly measured weight was administered. The body weights of the mice died during the test were excluded from statistical analysis. A death rate with respect to the concentration of MTX is represented by total number of mice survived in FIG. 7a and a death rate with respect to the concentration of the LDH-MTX hybrid is represented by the total number of mice survived in FIG. 7b. Referring to FIGS. 7a and 7b, $LD_{50}$ of MTX was 75 mg/kg, whereas $LD_{50}$ of the LDH-MTX hybrid was 25 mg/kg. That is, the lethal dose of the LDH-MTX hybrid was equal to ⅓ of that of MTX. Thus, considering that the anticancer effect of the LDH-MTX hybrid is 10 times higher than that of MTX as shown in FIG. 6a, the LDH-MTX hybrid can be effectively used in a smaller amount for anticancer therapy. This result shows that the LDH-MTX hybrid can be used as an injectable drug delivery system without having an adverse effect in vivo.

According to the present invention, Layered Double Hydroxide (LDH) can be used as a biocompatible injectable drug carrier that has little toxicity and adverse effect in vivo. Furthermore, LDH can also be used as a non-toxic injectable drug carrier maximizing drug efficacy and drug delivery efficiency when it is injected in vivo in the form of a hybrid with various drugs. In addition, LDH is suitable for use as an injectable drug carrier with regard to a particle size and shape. An actual animal test shows that LDH has no adverse effect in vivo on intraperitoneal application.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method for administering a drug delivery composition to a subject, comprising injecting into the subject the drug delivery composition, wherein the drug delivery composition comprises a drug carrier comprising a non-toxic, nano-size Layered Double Hydroxide (LDH) and a pharmaceutically acceptable excipients, and a drug.

2. The method of claim 1, wherein the LDH has a particle size of 100 to 300 nm.

3. The method of claim 1, wherein the drug is methotrexate (MTX).

4. The method of claim 1, the drug carrier is prepared by a method comprising 1) titrating a divalent and trivalent metal salts-containing aqueous solution with a base solution and incubating the resultant solution under hydrothermal synthesis condition to obtain LDH; and 2) controlling a particle size of the LDH.

5. The method of claim 4, wherein the divalent metal is selected from the group consisting of magnesium ($Mg^{2+}$), calcium ($Ca^{2+}$), and zinc ($Zn^{2+}$), and the trivalent metal is selected from the group consisting of aluminum ($Al^{3m+}$) and iron ($Fe^{3+}$).

6. The method of claim 4, wherein the base solution is selected from the group consisting of sodium hydroxide (NaOH) and ammonia ($NH_3$).

7. The method of claim 1, wherein the drug is loaded into the drug carrier by ion exchange or coprecipitation.

* * * * *